US010273510B2

(12) United States Patent
Tang et al.

(10) Patent No.: US 10,273,510 B2
(45) Date of Patent: Apr. 30, 2019

(54) EMULSION-BASED FERMENTATION FOR ACCELERATED GAS SUBSTRATE MASS TRANSFER

(71) Applicant: The Board of Trustees of the Leland Stanford Junior University, Stanford, CA (US)

(72) Inventors: Sindy Tang, Stanford, CA (US); Craig Criddle, Stanford, CA (US); Jaewook Myung, Stanford, CA (US); Minkyu Kim, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 58 days.

(21) Appl. No.: 15/418,337

(22) Filed: Jan. 27, 2017

(65) Prior Publication Data
US 2017/0218410 A1 Aug. 3, 2017

Related U.S. Application Data

(60) Provisional application No. 62/289,024, filed on Jan. 29, 2016.

(51) Int. Cl.
*C12P 7/62* (2006.01)
*C12N 1/20* (2006.01)
*C12N 1/26* (2006.01)

(52) U.S. Cl.
CPC .............. *C12P 7/625* (2013.01); *C12N 1/26* (2013.01); *Y02E 50/13* (2013.01)

(58) Field of Classification Search
None
See application file for complete search history.

(56) References Cited

U.S. PATENT DOCUMENTS 5,637,499 A * 6/1997 Turick .................. B01D 53/84
435/266
2010/0105112 A1 4/2010 Holtze et al.
(Continued)

FOREIGN PATENT DOCUMENTS

WO WO-2014194189 A1 * 12/2014 ............... C12N 1/20

OTHER PUBLICATIONS

Khmelenina, VN; et al; "Biosynthesis of Secondary Metabolites in Methanotrophs: Biochemical and Genetic Aspects (Review)" Applied Biochemistry and Microbiology, 51, 150-158, 2015 (Year: 2015).*
(Continued)

*Primary Examiner* — David W Berke-Schlessel
(74) *Attorney, Agent, or Firm* — Foley & Lardner LLP; Cliff Z. Liu

(57) ABSTRACT

Described here is a method for increasing the transfer of a gas substrate in microbial fermentation, comprising incubating an emulsion comprising an oil phase and an aqueous phase droplet dispersed in the oil phase, and supplying the gas substrate to the oil phase, wherein the aqueous phase droplet comprises a microorganism, and wherein the emulsion is stabilized by a surfactant or an amphiphilic particle that is adsorbed to an interface of the oil phase and the aqueous phase. Also described is an emulsion for microbial fermentation, comprises an oil phase and an aqueous phase droplet dispersed in the oil phase, wherein the aqueous phase droplet comprises a microorganism, wherein the emulsion comprises a gas substrate externally-supplied to the oil phase, and wherein the emulsion is stabilized by a surfactant or an amphiphilic particle that is adsorbed to an interface of the oil phase and the aqueous phase.

16 Claims, 4 Drawing Sheets

(56) References Cited

U.S. PATENT DOCUMENTS

2014/0069635 A1     3/2014    Cordiner
2016/0114325 A1     4/2016    Tang et al.

OTHER PUBLICATIONS

Pan, Ming; et al; "Fluorinated Pickering Emulsions Impede Interfacial Transport and Form Rigid Interface for the Growth of Anchorage-Dependent Cells" Applied Materials & Interfaces, 6, 21446-21453, 2014 (Year: 2014).*
Fei, Q. et al. (2014) "Bioconversion of natural gas to liquid fuel: Opportunities and challenges," Biotechnology Advances 32:596-614.
Holtze, C. et al. (2008) "Biocompatible surfactants for water-in-fluorocarbon emulsions," Lab Chip 8:1632-1639.
Junker, B.H. et al. (1990) "Oxygen transfer enhancement in aqueous/perfluorocarbon fermentation systems: I. experimental observations," Biotechnol. Bioeng. 35(6):578-585.
McMillan, J.D. et al. (1990) "Mechanisms of Oxygen Transfer Enhancement during Submerged Cultivation in Perfluorochemical-in-Water Dispersions," Ann. N.Y. Acad. Sci. 589:283-300.
Myung, J. et al. (2016) "Low energy emulsion-based fermentation enabling accelerated methane mass transfer and growth of poly(3-hydroxybutyrate)-accumulating methanotrophs," Bioresour Technol. 207:302-307.
Pan, M. et al. (2014) "Fluorinated pickering emulsions impede interfacial transport and form rigid interface for the growth of anchorage-dependent cells," ACS Appl. Mater. Interfaces 6:21446-21453.
Yoshida, F. et al. (1970) "Oxygen absorption into oil-in-water emulsions. A study on hydrocarbon fermenters," Ind. Eng. Chem. Process Des. Dev. 9:570-577.

* cited by examiner

EMULSION-BASED FERMENTATION FOR ACCELERATED GAS SUBSTRATE MASS TRANSFER

CROSS REFERENCE TO RELATED APPLICATION

This application claims the benefit of U.S. Provisional Application No. 62/289,024, filed Jan. 29, 2016, the content of which is incorporated herein by reference in its entirety.

BACKGROUND

Methane is an abundant gas emitted from both natural and anthropogenic sources. It is an excellent source of energy and heat via highly exothermic combustion. But from a biological perspective, methane also serves as a carbon and electron source for methane-utilizing bacteria (methanotrophs). Methanotrophs use methane as a sole or primary carbon source to mediate diverse natural processes including greenhouse gas mitigation, environmental remediation of pollutants and nitrogen cycling. In addition, methanotrophs are of great interest for their biotechnological applications. They can be used in biodiesel generation, propylene oxide production, single cell protein production, extracellular polysaccharides production, human health supplements production, and biological nitrogen removal. Also, researchers have developed methane-based poly(3-hydrobutyrate) (P3HB) biopolymer production processes using P3HB-accumulating methanotrophs (Type II methanotrophs).

An obstacle for methane-based bio-products, however, is the inefficient mass transfer of gases needed for high-density fermentations, as both methane and oxygen are sparingly soluble in the aqueous media used for methanotrophs growth. There is a strong connection between the rates of mass transfer, cell growth, and the production of desired products. To increase the mass transfer rates of sparingly soluble gases, bioreactors with vigorous mixing or agitation capabilities are typically used to create small gas bubbles that increase the gas-liquid interfacial area. The need for agitation inevitably increases the power demand and the operation cost. High shear rates from agitation can also damage cells and inhibit their growth.

SUMMARY

One aspect of some embodiments of the invention described herein relates to a method for increasing the transfer of a gas substrate in microbial fermentation, comprising incubating an emulsion comprising an oil phase and an aqueous phase droplet dispersed in the oil phase, and supplying the gas substrate to the oil phase, wherein the aqueous phase droplet comprises a microorganism, and wherein the emulsion is stabilized by a surfactant or an amphiphilic particle that is adsorbed to an interface of the oil phase and the aqueous phase.

In some embodiments, the gas substrate is alkane (e.g., methane). In some embodiments, the oil phase has a higher solubility for alkane (e.g., methane) than water.

In some embodiments, the gas substrate is carbon monoxide. In some embodiments, the oil phase has a higher solubility for carbon monoxide than water.

In some embodiments, the gas substrate is hydrogen. In some embodiments, the oil phase has a higher solubility for hydrogen than water.

In some embodiments, the aqueous phase droplet comprises an alkane utilizer (*Nocardia, Rhodococcus*, and *Gordonia*). In some embodiments, the aqueous phase droplet comprises a carbon monoxide utilizer (e.g., *Oligotropha, Pseudomonas, Bacillus, Streptomyces*, and *Mycobacterium*). In some embodiments, the aqueous phase droplet comprises a hydrogen utilizer (e.g., *Oligotropha, Pseudomonas, Bradyrhizobium, Bacillus, Streptomyces*, and *Mycobacterium*).

In some embodiments, the aqueous phase droplet comprises a carboxydotroph (see King et al., Nature Review Microbiology, 2007, 4:107-118). In some embodiments, the aqueous phase droplet comprises an alpha-proteobacteria. In some embodiments, the aqueous phase droplet comprises a firmicute. In some embodiments, the aqueous phase droplet comprises an actionbacteria. In some embodiments, the aqueous phase droplet comprises a gram-positive n-alkane degrader (see Quatrini et al., Journal of Applied Microbiology, 2008, 104:251-259).

In some embodiments, the aqueous phase droplet comprises a methanotroph. In some embodiments, the methanotroph is adapted to produce a polyhydroxyalkanoate. In some embodiments, the methanotroph is adapted to produce a poly-3-hydroxybutyrate (P3HB). In some embodiments, the method comprises supplying methane to the oil phase and fermenting a methanotroph in the aqueous phase.

In some embodiments, the methanotroph is adapted to produce a bioproduct of biodiesel generation, propylene oxide production, single cell protein production, extracellular polysaccharides production, or human health supplements production.

In some embodiments, the growth rate of a methanotroph in the emulsion of the present invention, in the absence of agitation, increases by at least 20%, or at least 50%, or at least 100%, or at least 200%, or at least 400%, after 48 hours of fermentation, compared with the growth rate of the methanotroph in a bulk aqueous solution where methane is delivered from the gas phase. In some embodiments, the growth rate of a methanotroph in the emulsion of the present invention, in the absence of agitation, increases by at least 20%, or at least 50%, or at least 100%, or at least 200%, or at least 400%, after 72 hours of fermentation, compared with the growth rate of the methanotroph in a bulk aqueous solution where methane is delivered from the gas phase. In some embodiments, the growth rate of a methanotroph in the emulsion of the present invention, in the absence of agitation, increases by at least 20%, or at least 50%, or at least 100%, or at least 200%, or at least 400%, after 96 hours of fermentation, compared with the growth rate of the methanotroph in a bulk aqueous solution where methane is delivered from the gas phase. In some embodiments, the growth rate of a methanotroph in the emulsion of the present invention, in the absence of agitation, increases by at least 20%, or at least 50%, or at least 100%, or at least 200%, or at least 400%, after 120 hours of fermentation, compared with the growth rate of the methanotroph in a bulk aqueous solution where methane is delivered from the gas phase.

In some embodiments, the amount of P3HB produced by a methanotroph in the emulsion of the present invention, in the absence of agitation, increases by at least 100%, or at least 2 times, or at least 5 times, or at least 10 times, or at least 20 times, or at least 50 times, after 48 hours of fermentation, compared with the amount of P3HB produced by the methanotroph in a bulk aqueous solution where methane is delivered from the gas phase. In some embodiments, the amount of P3HB produced by a methanotroph in the emulsion of the present invention, in the absence of agitation, increases by at least 100%, or at least 2 times, or at least 5 times, or at least 10 times, or at least 20 times, or at least 50 times, after 72 hours of fermentation, compared with the amount of P3HB produced by the methanotroph in a bulk aqueous solution where methane is delivered from the gas phase. In some embodiments, the amount of P3HB produced by a methanotroph in the emulsion of the present invention, in the absence of agitation, increases by at least 100%, or at least 2 times, or at least 5 times, or at least 10 times, or at least 20 times, or at least 50 times, after 96 hours of fermentation, compared with the amount of P3HB produced by the methanotroph in a bulk aqueous solution where methane is delivered from the gas phase. In some embodiments, the amount of P3HB produced by a methanotroph in the emulsion of the present invention, in the absence of agitation, increases by at least 100%, or at least 2 times, or at least 5 times, or at least 10 times, or at least 20 times, or at least 50 times, after 120 hours of fermentation, compared with the amount of P3HB produced by the methanotroph in a bulk aqueous solution where methane is delivered from the gas phase.

In some embodiments, the oil phase comprises a fluid that has a higher solubility for the gas substrate than the aqueous phase and is capable of generating a stable emulsion with the aqueous phase. In some embodiments, the oil phase comprises a hydrocarbon. In some embodiments, the oil phase comprises a fluorocarbon. In some embodiments, the oil phase is a fluorous phase. In some embodiments, the oil phase comprises at least one fluorinated solvent.

In some embodiments, the oil phase comprises at least one fluorocarbon represented by $C_xF_yH_zX_m$, where X can be any element (including but not restricted to N and O), and x, y, z, and m are positive integers. In some embodiments, the oil phase comprises HFE-7500 ($C_9H_5OF_{15}$), HFE-7600 ($C_8H_6OF_{12}$), FC-40 ($C_{21}F_{48}N_2$), perfluorohexane ($C_6F_{14}$), and/or perfluoromethyldecalin (PFMD or $C_{11}F_{20}$) as the fluorinated solvent. The fluorinated solvent is not particularly limited but can include a diverse range of fluorinated compounds having distinct physical properties. In some embodiments, the fluorinated solvent comprises a polar, partially fluorinated solvent with low viscosity, such as hydrofluoroethers like HFE-7500 and HFE-7600. In some embodiments, the fluorinated solvent comprises a polar, perfluorinated solvent with high viscosity, such as FC-40. In some embodiments, the fluorinated solvent comprises a non-polar, perfluorinated solvent with low viscosity, such as $C_6F_{14}$. In some embodiments, the fluorinated solvent comprises a non-polar perfluorinated solvent with high viscosity, such as PFMD.

In some embodiments, the dispersed aqueous phase has an average diameter greater than or equal to about 50 nm and less than or equal to about 1000 microns. In some embodiments, the dispersed aqueous phase has an average diameter of no more than about 1000 microns. In some embodiments, the dispersed aqueous phase has an average diameter greater than or equal to about 50 nm. In some embodiments, the dispersed aqueous phase does not coalesce for at least 30 minutes at 25° C. and 1 atm. In some embodiments, the dispersed aqueous phase comprises nutrients and/or substrates for microbial fermentation.

In some embodiments, the emulsion is stabilized by a surfactant. In some embodiments, the emulsion is stabilized by a nonionic fluoro-surfactant based on PEG-PFPE amphiphilic block copolymer (also referred to as "EA-surfactant" from RainDance Technologies). EA-surfactants are described in U.S. Pat. No. 9,012,390, which is incorporated herein by reference in its entirety.

In some embodiments, the emulsion is stabilized by partially fluorinated amphiphilic nanoparticles, which are described in U.S. Pat. Pub. No. 2016/0114325, which is incorporated herein by reference in its entirety. The partially fluorinated amphiphilic particles can include both homogeneous particles and Janus particles where the surface has two or more distinct physical and/or chemical properties.

In some embodiments, the amphiphilic particles are ceramic nanoparticles or microparticles, metal nanoparticles or microparticles, polymeric nanoparticles or microparticles, or semiconductor nanoparticles or microparticles, or a combination thereof. In some embodiments, the amphiphilic particles are silica nanoparticles or microparticles. In some embodiments, other particles that have functionalizable surfaces and can be rendered amphiphilic are also compatible with embodiments of the invention described herein, such as particles made from noble metals, semiconductors or organic polymers.

In some embodiments, at least 50% (e.g., by number or weight), at least 70%, at least 80%, at least 90%, or at least 95% of the nanoparticles and/or microparticles of the emulsion are amphiphilic particles. In some embodiments, at least 50% (e.g., by number or weight), at least 70%, at least 80%, at least 90%, or at least 95% of the nanoparticles and/or microparticles of the emulsion are amphiphilic silica nanoparticles.

The amphiphilic nature of the particles described herein (e.g., silica nanoparticles) is evident from the three phase contact angle θ when they are placed at an interface of a fluorous oil phase and a water phase. In some embodiments, the amphiphilic particles have a contact angle θ of about 90° to 150° at an interface of a fluorous oil phase and a water phase. In some embodiments, the amphiphilic particles have a contact angle θ of about 90° to 135° at an interface of a fluorous oil phase and a water phase. In some embodiments, the amphiphilic particles have a contact angle θ of about 90° to 120° at an interface of a fluorous oil phase and a water phase. In some embodiments, the amphiphilic particles have a contact angle θ of about 100° to 110° at an interface of a fluorous oil phase and a water phase.

In some embodiments, at least 50%, at least 70%, at least 80%, at least 90%, or at least 95% of the amphiphilic particles of the emulsion, when placed at an interface of a fluorous oil phase and a water phase, have a contact angle θ of about 90° to 150°. In some embodiments, at least 50%, at least 70%, at least 80%, at least 90%, or at least 95% of the amphiphilic particles of the emulsion, when placed at an interface of a fluorous oil phase and a water phase, have a contact angle θ of about 90° to 135°. In some embodiments, at least 50%, at least 70%, at least 80%, at least 90%, or at least 95% of the amphiphilic particles of the emulsion, when placed at an interface of a fluorous oil phase and a water phase, have a contact angle θ of about 90° to 120°. In some embodiments, at least 50%, at least 70%, at least 80%, at least 90%, or at least 95% of the amphiphilic particles of the emulsion, when placed at an interface of a fluorous oil phase and a water phase, have a contact angle θ of about 100° to 110°.

In some embodiments, the amphiphilic particle has at least one lateral dimension of 0.001-1000 microns. In some embodiments, the amphiphilic particle has at least one lateral dimension of 0.01-100 microns, or 0.1-10 microns, or 1-5000 nm, or 10-950 nm, or 20-200 nm, or 200-800 nm. In some embodiments, the amphiphilic particle has a size that will not cause clogging in microfluidic devices and/or sedimentations (for prolonged time) in syringes, such as 50-200 nm. In some embodiments, same mass of particles gives higher concentration in terms of particle number per volume. Microparticles larger than 5 microns can also be used.

In some embodiments, the amphiphilic particle comprises fluorinated groups covalently bonded on the surface of the particle. In some embodiments, the amphiphilic particle comprises fluorinated hydrocarbon groups bonded on the surface of the particle, such as fluorinated alkyl groups bonded on the surface of the particle. Examples of fluorinated hydrocarbon groups include C1-C20, C2-C20, C5-C20, C10-C20, C1-C15, C2-C15, C5-C15, C10-C15, C1-C10, C2-C10, C5-C10, and C5-C8 hydrocarbon groups, substituted with 1 or more, 2 or more, 3 or more, 4 or more, 5 or more, 6 or more, 7 or more, 8 or more, 9 or more, 10 or more, 11 or more, 12 or more, or 13 or more fluorine atoms per hydrocarbon group. Other types of halogenated hydrocarbon groups are also contemplated. In some embodiments, the amphiphilic particle is partially derivatized with at least one partially fluorinated or perfluorinated alkyl-silane. In some embodiments, the amphiphilic particle is partially derivatized with at least one partially fluorinated or perfluorinated alkyl-silane comprising a linear carbon chain. In some embodiments, the amphiphilic particle is partially derivatized with 1H, 1H, 2H, 2H-perfluorooctyltriethoxysilane (FAS) on the surface.

In some embodiments, the amphiphilic particle comprises hydrophilic groups, in addition to or in place of fluorinated groups, covalently bonded on the surface of the particle. In some embodiments, the amphiphilic particle comprises amine groups covalently bonded on the surface of the particle. In some embodiments, the amphiphilic particle comprises other chemical groups covalently bonded on the surface of the particle, including but not restricted to —OH, —COOH, —NH$_2$, —C$_x$H$_y$, —SO$_3$H, fluorophores such as fluorescein, rhodamine, macromolecules such as biotin, streptavidin, and polyethylene glycol (PEG).

In some embodiments, the amphiphilic particles on average have at least 30% of their outer surface areas fluorinated/derivatized. In some embodiments, the amphiphilic particles on average have at least 40%, or at least 50%, or at least 60%, or at least 70%, or at least 80%, or at least 90%, or up to 100% of their outer surface areas fluorinated/derivatized. The partially fluorinated amphiphilic particles include both homogeneous particles and Janus particles where the surface has two or more distinct physical and chemical properties.

In some embodiments, the emulsion comprises a mixture of amphiphilic particles having different sizes and chemistry.

In some embodiments, the amphiphilic particles have high temperature stability. In some embodiments, the amphiphilic particles are substantially stable after heating at 95° C. for at least 20 minutes, or at least 30 minutes, or at least 60 minutes. In some embodiments, the amphiphilic particles are substantially stable after heating at 150° C. for at least 20 minutes, or at least 30 minutes, or at least 60 minutes. In some embodiments, the amphiphilic particles are substantially stable after heating at 200° C. for at least 20 minutes, or at least 30 minutes, or at least 60 minutes.

In some embodiments, the amphiphilic particles have a spherical shape. In some embodiments, the amphiphilic particles have an elliptical shape. In some embodiments, the amphiphilic particles have a rod-like shape. In some embodiments, the amphiphilic particles have a plate-like shape.

In some embodiments, the aqueous phase further comprises a hydrophilic polymer adsorbed to the amphiphilic particle at the interface. The hydrophilic polymer (e.g., PEG) can be pre-dispersed in the aqueous phase, while amphiphilic particle (e.g., partially fluorinated silica nanoparticle) can be pre-dispersed in the oil phase. As the water-in-oil emulsion is generated, the amphiphilic particle adsorbs to the water-oil interface and the hydrophilic polymer adsorbs onto the surface of the amphiphilic particle from within the aqueous phase droplet.

In some embodiments, the hydrophilic polymer is covalently grafted onto the amphiphilic particle. The amphiphilic particle covalently grafted with the hydrophilic polymer can be pre-dispersed into the oil phase when generating the emulsion.

In some embodiments, the hydrophilic polymer is not covalently linked to the amphiphilic particle.

In some embodiments, the hydrophilic polymer is polyethylene glycol (PEG). Other embodiments of the hydrophilic polymers include polyelectrolytes and non-ionic polymers such as homopolymers (e.g., polyethers, polyacrylamide (PAM), polyethylenimine (PEI), poly(acrylic acid), polymethacrylate and other acrylic polymers, poly(vinyl alcohol) (PVA), and poly(vinylpyrrolidone) (PVP)), and block co-polymers.

In some embodiments, the aqueous phase comprises 0.01 mg/mL or more, or 0.02 mg/mL or more, or 0.05 mg/mL or more, or 0.1 mg/mL or more, or 0.2 mg/mL or more, or 0.5 mg/mL or more, or 1 mg/mL or more, or 2 mg/mL or more, or 5 mg/mL or more, or 10 mg/mL or more of a hydrophilic polymer (e.g., PEG). In some embodiments, the aqueous phase comprises an effective amount of a hydrophilic polymer (e.g., PEG) for preventing adhesion of cells to the droplet interface.

In some embodiments, the method is substantially free of mechanical stirring or agitation of the emulsion during incubation.

Another aspect of some embodiments of the invention described herein relates to an emulsion for microbial fermentation, comprises an oil phase and an aqueous phase droplet dispersed in the oil phase, wherein the aqueous phase droplet comprises a microorganism, wherein the emulsion comprises a gas substrate externally-supplied to the oil phase, and wherein the emulsion is stabilized by a surfactant or a nanoparticle that is adsorbed to an interface of the oil phase and the aqueous phase. In some embodiments, the aqueous phase droplet comprises a methanotroph, and the emulsion comprises methane externally-supplied to the oil phase.

A further aspect of some embodiments of the invention described herein relates to a method for obtaining an emulsion for microbial fermentation, comprising mixing an oil phase and an aqueous phase, wherein the oil phase comprises (a) a fluorocarbon and (b) a surfactant or a nanoparticle adapted to adsorb to an interface of the oil phase and the aqueous phase, and wherein the aqueous phase comprises a microorganism and optionally a hydrophilic polymer. In some embodiments, the aqueous phase comprises a methanotroph.

These and other features, together with the organization and manner of operation thereof, will become apparent from the following detailed description when taken in conjunction with the accompanying drawings.

Figure 3:
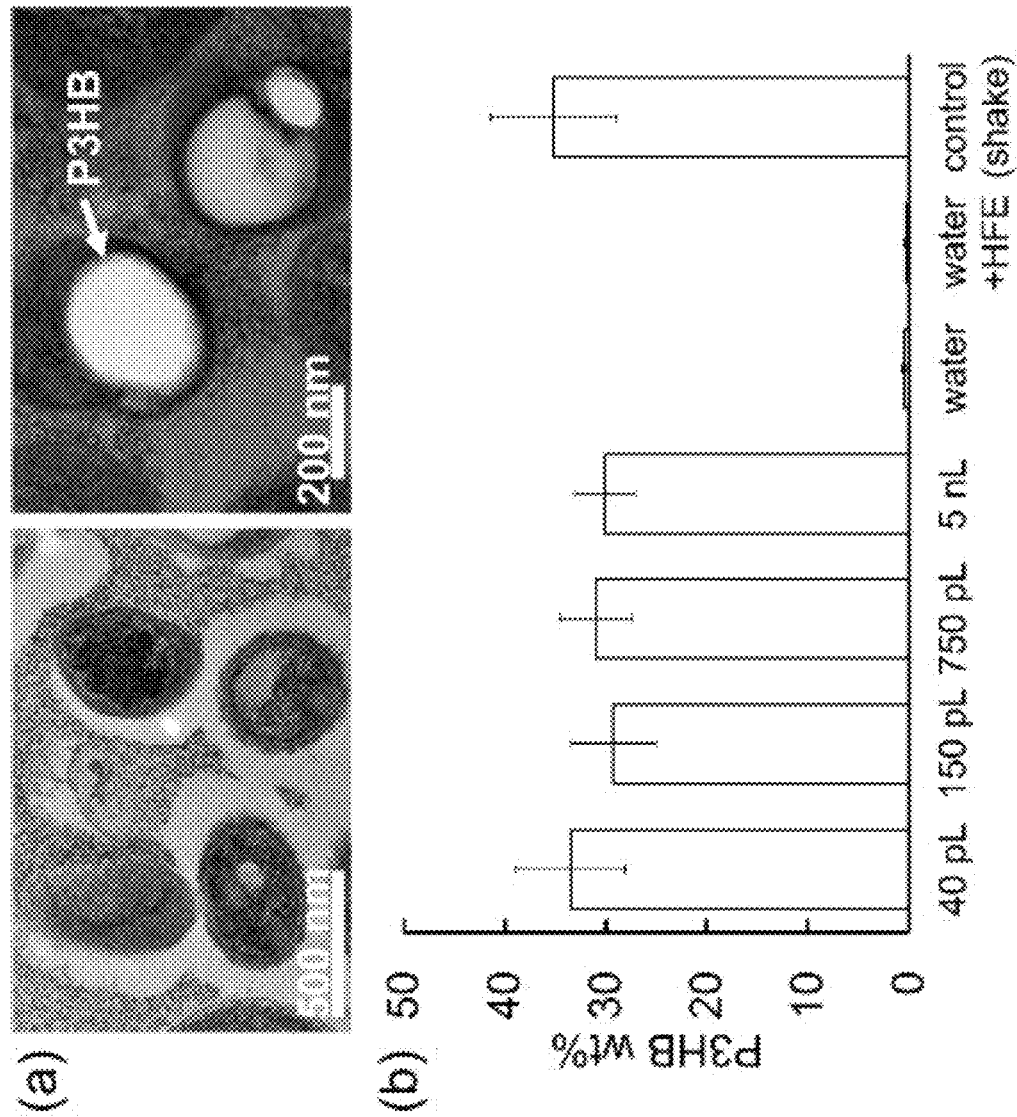

FIG. 3: Comparison of P3HB accumulation in cells grown in bulk solution and cells grown in droplets after seven days of incubation. (a) TEM images. (b) P3HB wt % as measured by Nile red stain.

Figure 4:
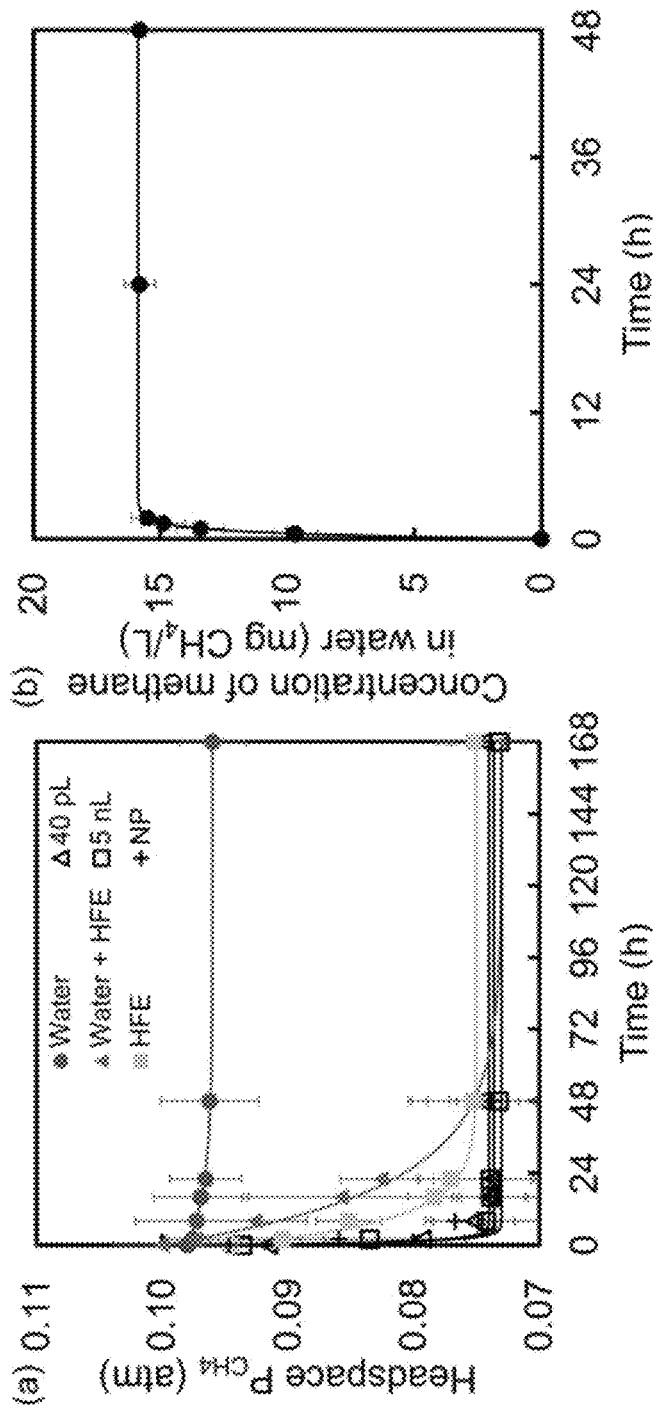

FIG. 4: (a) Partitioning of methane from gas phase to liquid phase in the absence of microbial growth. Lines in the figure were modelled using Eq. (1). For all experiments, the volume of water and HFE were kept constant at 1.8 mL (except in the sample that contained water only). The volume of the gas phase was 4.4 mL. (b) Partitioning of methane from methane-saturated HFE to water. The volume of water and HFE were both 4.0 mL.

DETAILED DESCRIPTION

In some embodiments, describe here is a method for accelerating methane mass transfer without the need for agitation. This effect can be achieved by growing methanotrophs in water-in-oil (W/O) emulsions suspended in an oil that has a higher solubility for methane than water does. The method provides enhanced mass transfer of methane or P3HB accumulation within an emulsion-based system. Here a fluorinated oil with biocompatibility was used, gas permeability and corresponding emulsion stabilizing agents were used to generate stable emulsions. Other oils can also be used so long as they possess similar qualities. For example, hydrocarbon-based oils having a higher solubility for methane than water and being capable of generating a stable emulsion can be used. It is shown that the growth rate of methanotrophs in such emulsions, in the absence of agitation, may increase by, for example, four to five times compared with growth rates in bulk aqueous solution where methane is delivered from the gas phase. It is found that cells incubated in the emulsions can accumulate, for example, up to 67 times more P3HB than in bulk within seven days. Emulsion-based fermentation thus can be used for high-density methanotroph fermentations.

Volumes of Droplets Generated.

Figure 1:
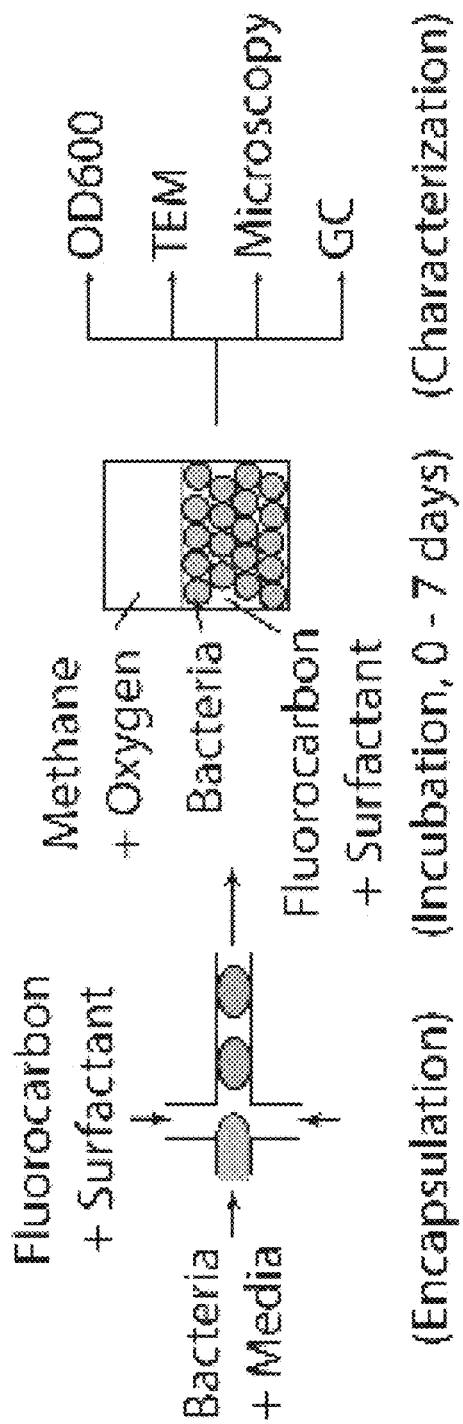
FIG. 1: Scheme of an example microfluidic device and process flow.

As shown in FIG. 1, cells suspended in the culture media were encapsulated into microdroplets. To generate uniform drops of different volumes, the flow rates of continuous and disperse phases were varied, and the geometry of flow-focusing nozzle. To generate polydisperse drops, the culture media were mixed with the continuous phase followed by manual shaking. The size of the drops obtained ranged from 5 pL to 1 nL. The drops generated were then collected in a gas-tight vial and incubated with methane and oxygen injected in the headspace. Small volumes of the drops were sampled and destabilized for the characterization of cell growth and P3HB accumulation at various time points.

The Rate of Cell Growth Increased in Emulsion-Based Fermentation.

FIG. 2*a* shows bright-field microscopy images of cells in 40 pL drops as a function of time. At the initial concentration of cells used ($OD_{600}$~0.1, corresponding to ~$9.28 \times 10^7$ cells/mL), a 40-pL drop contained an average of 4 cells at t=0 h. The number of cells in a drop increased significantly after 48 h. No further increase was observed after 96 h. The qualitative trend of cell growth from these microcopy images was consistent with optical density measurements. FIG. 2*b* shows that cells replicated rapidly during the first 72 h to reach $OD_{600}$~0.7 (corresponding to $6.50 \times 10^8$ cells/mL) and stabilized afterwards. In the control experiment where the cells were cultured with shaking at 150 rpm in the aqueous media without HFE-7500 or emulsions, the cells also grew to a maximum density of $OD_{600}$~0.7 in 72 h. The encapsulation of cells in emulsions thus did not have negative effect on the growth rate and final cell density reached. The observed time scale for cell growth was expected based on the composition of the culture media. The composition of the media was chosen such that nitrogen (ammonium) was the limiting nutrient. Nitrogen depletion is generally considered an effective trigger to start P3HB accumulation in methanotrophic bacteria. The amount of nitrogen used in the media was also designed to allow the growth of methanotrophs for three days, after which the cells switch to P3HB accumulation mode.

In the absence of agitation, the use of emulsions increased the rate of cell growth compared with growth in bulk solution. FIG. 2*b* shows that the cell density obtained from growth in emulsions was ~2.2 times more than that in bulk media at t=168 hours. The maximum rate of growth (as measured by the biggest increase in $OD_{600}$ between two time points $[\Delta OD_{600}/\Delta t]max$) increased by 4.6±0.4 times when the cells were incubated in emulsions, compared with their growth in bulk media and in a mixture of bulk media and neat HFE-7500 without the formation of emulsion. Previously, a small amount of paraffin oil (2.5-10% v/v) was added to the aqueous bulk media to increase the mass transfer of methane. As paraffin oil has a higher solubility of methane than water does, an increased cell density was obtained compared with the case without paraffin oil when the incubation was performed with shaking at 150 rpm. In the absence of shaking, however, the results show that the addition of an immiscible phase (HFE-7500) having a higher methane solubility alone was insufficient to increase the rate of cell growth. Due to the relatively high interfacial tension (~50 mN/m) between water and HFE-7500, the mixture separated into top and bottom phases spontaneously with no agitation. Such mixture would at most double the interfacial area and the corresponding mass transfer between the aqueous phase and HFE-7500 or the gas phase in the headspace. On the other hand, the use of emulsions stabilized by surfactants or NPs increased the interfacial area between HFE-7500 and the aqueous phase significantly. For the size of drops used here, the interfacial area increased by approximately 160-800 times compared with bulk solution. So long as the emulsions were stable against coalescence, no shaking was required to maintain this large interfacial area for enhanced mass transfer of methane into the aqueous phase. Surprisingly, no noticeable difference in growth rates was observed in emulsions composed of monodisperse drops for the volumes tested and in polydisperse drops with volumes ranging from 5 pL to 5 nL, whether stabilized by surfactants or NPs, as shown in FIG. 4.

P3HB Accumulation Increased in Emulsion-Based Fermentation.

Based on cell growth data, it is expect that cells grown in emulsions would accumulate more P3HB than cells in bulk media do in the absence of agitation. Indeed, FIG. 3 shows that cells grown inside droplets accumulated ~32±4 wt % P3HB while cells grown in bulk media did not accumulate any P3HB, as indicated by both TEM images and Nile red staining. In the control experiment where the cells were cultured with shaking at 150 rpm in aqueous media without HFE-7500 or emulsions, the maximum amount of P3HB accumulated was ~35±6 wt % of cell mass. As such, the emulsion was effective in increasing the rate of accumulation of P3HB with no significant effect on the final accumulated level of P3HB.

Emulsion-Based Fermentation is Limited by Methane Consumption Rather than Mass Transfer.

Figure 2:
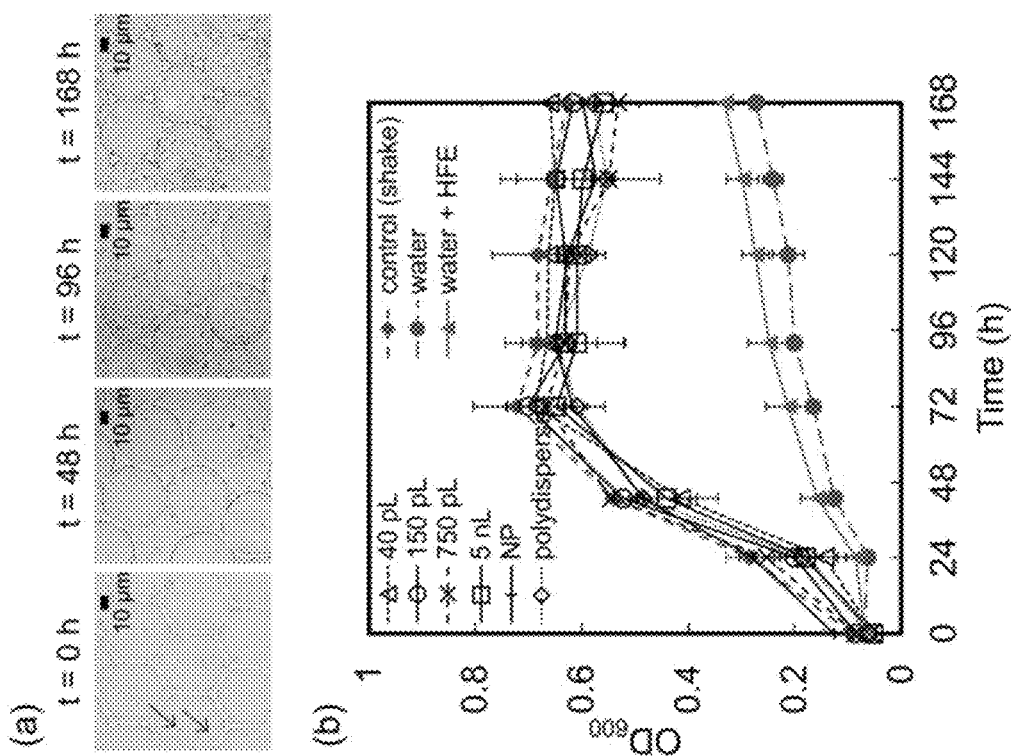
FIG. 2: Cell growth in drops. (a) Bright-field microscopy images of 40-pL drops containing cells at different time points. Arrows indicate two cells in the drop at t=0 h. (b) Comparison of OD600 of culture grown in emulsions composed of monodisperse drops (40 pL, 150 pL, 750 pL and 5 nL), polydisperse drops, polydisperse drops stabilized by NPs, bulk aqueous media, and bulk aqueous media mixed with HFE-7500 containing no emulsions. In each sample, the total volumes of the aqueous media and HFE-7500 were fixed at 1.8 mL respectively except for the samples containing aqueous media only. All experiments were performed with no shaking except the control. The control composed of 1.8-mL aqueous media under shaking conditions at 150 rpm.

FIGS. 2 and 3 show that the size of the drops used did not affect cell growth or P3HB accumulation. These results indicate that the culture may be rate-limited by cell metabolism, rather than the mass transport of methane. To verify this effect, the kinetics of mass transfer of methane from the gas phase into the liquid phase were measured. FIG. 4a shows the partial pressure of methane in the headspace of water and HFE-7500 respectively over 168 hours. The initial and equilibrium partial pressures of methane in the headspace were used to calculate the Henry's constant for quantifying the solubility of methane in different liquids. The Henry's constant calculated for HFE-7500 ($1.1 \times 10^{-2}$ mol atm$^{-1}$) was about 10 times higher than that for water ($1.2 \times 10^{-3}$ mol atm$^{-1}$). Methane is thus approximately 10 times more soluble in HFE-7500 than in water. The curves in FIG. 4a also allowed us to calculate the rate of methane transfer from the gas phase to the liquid phase using Eq. (1):

$$\frac{dC}{dt} = K_L a (C^* - C) \quad (1)$$

where $$C = \frac{V_{gas}}{V_{liquid} RT}(P_0 - P)$$

is the concentration of dissolved methane in the liquid phase (mg CH$_4$ L$^{-1}$), $V_{gas}$ is the volume of gas in the headspace, $V_{liquid}$ is the volume of the liquid, R is the universal gas constant, T is temperature, P is the partial pressure of methane at time t, and $P_0$ is the partial pressure of methane at time t=0. $C^*$ is the saturated concentration of dissolved methane (mg CH$_4$ L$^{-1}$), $K_L$ is the mass transfer coefficient (cm h$^{-1}$) and a is the gas/liquid interfacial area per volume of liquid (cm$^2$ cm$^{-3}$). Because of the difficulty in measuring $K_L$ and a separately, the product $K_L a$ is treated as a single measurable variable representing the volumetric mass transfer coefficient. Integrating Eq. (1) yields Eq. (2):

$$\ln\left(1 - \frac{C}{C^*}\right) = -K_L a t \quad (2)$$

$K_L a$ for different liquids in FIG. 4a were found readily from the slope of Eq. (2) (Table 1). The $K_L a$ of methane from HFE-7500 to water was found using a similar procedure (FIG. 4b, Table 1). The effective $K_L a$ from the gas phase into the emulsions was then estimated. Briefly, the emulsion system can be treated as a three-phase system where methane has to be transported, in series, from the gas phase to the oil phase (HFE-7500) and then into the aqueous phase. A resistance-in-series model is applied to estimate the total resistance to mass transfer, which equals the sum of the resistances at the gas-HFE and HFE-water interfaces. The overall mass transfer coefficient is the reciprocal of the overall resistance.

TABLE 1

$K_L a$ values for different liquids tested.

| Liquids | $K_L a$ (h$^{-1}$) |
|---|---|
| Water + HFE-7500 | 0.051 |
| Water | 0.051 |
| HFE-7500 | 0.115 |
| Emulsion composed of 40 pL drops stabilized by surfactants | 1.149 |
| Emulsion composed of 5 nL drops stabilized by surfactants | 1.146 |
| Emulsion composed of polydisperse drops stabilized by NP | 1.147 |

To identify whether mass transfer or cell metabolism was the rate limiting step in cell growth, the Damköhler number (Da) were calculated. Da is a dimensionless number that characterizes the reaction rate relative to the transport rate, and is defined as maximum possible methane utilization rate (MUR$_{max}$) divided by the maximum mass transfer rate (MTR$_{max}$):

$$Da = \frac{MUR_{max}}{MTR_{max}} = \frac{q_{max,CH4} X}{K_L a [CH_4]^*} \quad (3)$$

where $q_{max,CH4}$ is the specific methane utilization rate, X is the average cell concentration measured throughout the seven days of incubation, and [CH4]* is the saturation concentration of CH4 in the aqueous media. The value of $q_{max,CH4}$ were measured to be 0.044 mg CH$^4$ mg TSS-1 h$^{-1}$. The average Da numbers calculated for water (Da=8.1) and water and HFE-7500 without surfactant (Da=8.7) were both higher than 1, which indicate that cell growth was mass-transfer limited. On the other hand, the average Da numbers calculated for emulsions composed of drops of volumes 5 nL (Da=0.62), 40 pL (Da=0.62) and NP-stabilized polydisperse droplets (Da=0.63) were all less than 1, which indicate that cell growth was limited by reaction-rate or cell metabolism. These values also explain why no significant differences were observed when drops of different sizes were used in FIGS. 2 and 3. The lack of dependence on droplet size and uniformity allows the use of emulsification techniques that are more easily scalable than microfluidic approach. Indeed, the use of polydisperse emulsions formed by manual shaking gave similar results as monodisperse emulsions did. Furthermore, replacing surfactants with NPs rendered similar results. The use of NPs as stabilizers is advantageous because NPs are cheaper than surfactants, and can be potentially recovered and reused more easily than surfactants.

Scaling-Up of the Emulsion-Based Fermentation.

In moving towards the scaling-up of the emulsion method shown here, further optimization can be implemented to destabilize the emulsion by applying an electric field. As the addition of chemical destabilizers is not necessary in this case, the oil phase and the NPs used for stabilizing the emulsion can be recycled to reduce cost and waste reagents. Although a single type of oil was used in this embodiment, the principle can be applied to other oils that are potentially more cost-effective and environmentally friendly than HFE-7500, so long as they satisfy the following: (1) compatibility with the growth of methanotrophs; (2) high solubility of methane, and low mass transfer resistance with the gas phase and with the water phase respectively; and (3) availability of the corresponding emulsion stabilizing agents. The emulsion-based method shown here can be used for the high-density production of P3HB from methanotrophs.

It has been demonstrated an emulsion-based fermentation method for increasing the rates of cell growth and P3HB accumulation without the need for agitation. The use of emulsion effectively increased the interfacial area of the aqueous phase to accelerate the mass transfer of methane. The fermentation process became rate-limited by cell metabolism rather than the mass transport of methane. The use of microfluidics did not negatively affect cell growth and P3HB accumulation.

WORKING EXAMPLES

Example 1.1—Culture Conditions

*Methylocystis parvus* OBBP, a P3HB-producing Type II methanotrophs, was used for all experiments in this study. *M. parvus* OBBP was grown in medium JM2. JM2 contained the following chemicals per liter of solution: 2.4 mM $MgSO_4 \cdot 7H_2O$, 0.26 mM $CaCl_2$, 36 mM $NaHCO_3$, 4.8 mM $KH_2PO_4$, 6.8 mM $K_2HPO_4$, 10.5 µM $Na_2MoO_4 \cdot 2H_2O$, 7 µM $CuSO_4 \cdot 5H_2O$, 200 µM Fe-EDTA, 530 µM Ca-EDTA, 5 mL trace metal solution and 20 mL vitamin solution. The trace metal stock solution contained the following chemicals per liter of solution: 500 mg $FeSO_4 \cdot 7H_2O$, 400 mg $ZnSO_4 \cdot 7H_2O$, 20 mg $MnCl_2 \cdot 7H_2O$, 50 mg $CoCl_2 \cdot 6H_2O$, 10 mg $NiCl_2 \cdot 6H_2O$, 15 mg $H_3BO_3$ and 250 mg EDTA. The vitamin stock solution contained the following chemicals per liter of solution: 2.0 mg biotin, 2.0 mg folic acid, 5.0 mg thiamine.HC1, 5.0 mg calcium pantothenate, 0.1 mg vitamin B12, 5.0 mg riboflavin and 5.0 mg nicotinamide. Ammonium chloride (4 mM) was added as a nitrogen source. *M. parvus* OBBP was grown in this liquid culture to reach an exponential phase with an optical density ($OD_{600}$) of approximately 0.1. This concentration of cells was used in all subsequent experiments.

Example 1.2—Generation of Emulsions

Microfluidic flow-focusing devices were used for the generation of emulsions composed of uniform microdroplets with controlled volumes. Soft lithography were used to fabricate microfluidic channels in poly(dimethylsiloxane) (PDMS). The microchannels were rendered hydrophobic by treatment with Aquapel (Pittsburgh Glass Works LLC, Pittsburgh, Pa., USA) to avoid droplet wetting of the wall. The droplets generated had a size dispersity<5%. The continuous phase was a hydrofluoroether HFE-7500 (3M, St. Paul, Minn., USA) containing a biocompatible "EA-surfactant" (RAN Biotechnologies Inc., Beverly, Mass., USA) (2% w/w), a PEG-PFPE amphiphilic block copolymer, to stabilize the drops against coalescence. These drops were stable for weeks. HFE-7500 was inert and permeable to gases, and had been shown to be compatible with cell cultures in drops. To study the effect of droplet size on the growth rate of the cells and the accumulation of P3HB, four different sizes of droplets were generated ranging from 40 pL to 5 nL in volume.

For the generation of emulsions composed of polydisperse drops, vigorous shaking of a mixture was manually performed of bacterial media (*M. parvus* OBBP culture, OD600~0.1) and HFE-7500 containing EA-surfactant (2% w/w) at 2:3 volume ratio for 1 min. The size distribution of the drops formed was characterized. 100 nm amphiphilic silica nanoparticles (NPs) were also used to replace EA-surfactant for stabilizing the drops. The synthesis of these NPs was described in Examples 1.1. To prevent the adhesion of cells to NP surface, polyethylene glycol (MW=8000, 10 mg/mL) were also introduced into the aqueous phase prior to droplet formation.

As water has a lower density than HFE-7500 does (p=1.63 g/mL), the generated drops creamed to the top of the collection vial to form a concentrated emulsion with volume fraction φ ~80% within minutes upon collection. The volume fraction φ is defined as $\varphi = V_{aq}/V_{oil}$, where $V_{aq}$ is the total volume of the aqueous drops, and $V_{oil}$ is the volume of the HFE-7500 containing surfactants or NPs. For all subsequent experiments, 1.8 mL of this concentrated emulsion (φ ~80%) was collected into a gas-tight glass vial (Wheaton, Mealville, N.J., USA) capped with butyl-rubber stoppers which were then crimp-sealed. The headspace in each vial was over-pressured at approximately 1.5 atm with 1:1.5 molar ratio of methane and oxygen. The emulsion was incubated at 30° C. for 0-7 days without shaking.

Example 1.3—Optical Density Measurements and Imaging of Cells in Drops

To measure the optical density ($OD_{600}$) of the cells, the emulsions were destabilized by adding 200 µL of 1H,1H, 2H,2H-perfluorooctanol (Sigma-Aldrich, St Louis, Mo., USA) to each 200 µL of emulsion to merge the droplets into a single aqueous phase. For NP-stabilized drops, 300 µL of fluorinert FC-40 (Sigma-Aldrich, St Louis, Mo., USA) was added to destabilize 50 µL of the emulsion. For imaging the cells within the drops, the drops were injected into a wide microfluidic channel and imaged using an inverted optical microscope and an Electron Multiplying Charge Coupled Device (Andor iXon Ultra 897, Andor Technology Ltd., Belfast, UK).

Example 1.4—Visualization and Quantification of P3HB

Transmission electron microscopy (TEM) was used to evaluate the morphology of the P3HB granules. After seven days of incubation, bacterial pellets were fixed with 2% glutaraldehyde and 4% paraformaldehyde in 0.1 M sodium cacodylate buffer ($Na(CH_3)_2AsO_2 \cdot 3H_2O$), pH 7.4 for 48 h at 4° C. To coat cells in gelatin, cells were washed in the buffer and resuspended in 10% warm (~50° C.) gelatin for 5 min, placed on ice for 5 min, then cut into blocks and post-fixed using cold osmium tetroxide ($OsO_4$). Post-fixed samples were dehydrated using ethanol and acetonitrile, embedded in an epoxy resin mixture, then cut into ultra-thin sections, which were then mounted on copper grids. The grids were observed with a JEOL TEM 1400 microscope equipped with a Gatan 967 slow-scan, cooled CCD camera. Images were processed using Digital Micrograph, Digital Montage and TEM Auto tune.

To quantify P3HB content accumulated in the cells, Nile red was used to stain P3HB in the cells following a protocol published previously. Nile red staining requires small amounts of cells (<0.1 mg), and has been demonstrated to be a reliable method for measuring P3HB level in methanotrophs. Fluorescence intensity was measured from the cells after Nile red staining using a Scanford flow cytometer and 561 nm laser. The corresponding P3HB concentration (mg P3HB mg $TSS^{-1}$) was then extracted by comparing the measured fluorescence intensity with a calibration curve obtained previously. The calibration showed linear relationship between Nile red fluorescence intensity and P3HB content in cells (mg P3HB mg TSS$^{-1}$) as measured by gas chromatography equipped with a flame ionization detector (GC-FID).

Example 1.5—Measurement of Methane Solubility and Partitioning Kinetics from Gas Phase to Liquid Phase To measure the solubility of methane in various liquids, the partial pressure of methane was monitored in the headspace of water, HFE-7500 and the emulsions ($\varphi$~80%) respectively. Methane was injected in the headspace (4.4 mL) of a glass vial containing these liquids at a fixed volume of 3.6 mL. All vials were subject to same conditions at 30° C. To measure the concentration of methane, 0.5 mL of gas was extracted from the headspace and injected into a GOW-MAC gas chromatograph (GOW-Mac Instrument Co., Bethlehem, Pa., USA) with an Alltech CTR 1 column (Alltech Associates Inc., Deerfield, Ill., USA) and a thermal conductivity detector. The following parameters were used: injector, 120° C.; column, 60° C.; detector, 120° C.; and current, 150 mV. Peak areas of methane were compared to standards and quantified using the software ChromPerfect (Justice Laboratory Software, Denville, N.J., USA).

Example 1.6—Measurement of Methane Partitioning Kinetics from HFE-7500 to Water

To determine the methane partitioning kinetics between HFE-7500 and water, 4.0 mL of HFE-7500 was first saturated with methane by injection into a gas-tight glass vial (Wheaton, Mealville, N.J., USA) filled with 100% methane in the headspace. After saturation, HFE-7500 was added to separate bottles containing 4.0 mL of water and a vacuum headspace, allowing HFE-7500 to fill the vacant volume. All vials were subject to same conditions at 30° C. To measure the concentration of methane in water, 2.0 mL of methane-dissolved water was sampled using a syringe needle, and the chemical oxygen demand (COD) of the water sample was analyzed using a test kit (COD Reagent, TNT Plus, ULR; Hach Company, Loveland, Colo., USA).

Example 1.7—Measurement of Maximum Specific Methane Utilization Rate

The maximum specific methane utilization rate ($q_{max,CH4}$) for *M. parvus* OBBP in the culture media was evaluated. Briefly, cells were incubated in 160-mL serum bottle (Wheaton, Mealville, N.J., USA) capped with butyl-rubber stoppers and crimp-sealed under excess $CH_4$:$O_2$ headspace (molar ratio of 1:1.5). All bottles were incubated horizontally on orbital shaker tables at 150 rpm. The incubation temperature was 30° C. Bottle headspace was analyzed periodically to evaluate methane consumption.

As used herein, the singular terms "a," "an," and "the" include plural referents unless the context clearly dictates otherwise. Thus, for example, reference to a molecule can include multiple molecules unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A method for increasing the transfer of a gas substrate in microbial fermentation, comprising incubating an emulsion comprising an oil phase and an aqueous phase droplet dispersed in the oil phase, and supplying the gas substrate to the oil phase, wherein the aqueous phase droplet comprises a microorganism, and wherein the emulsion is stabilized by a surfactant or an amphiphilic particle that is adsorbed to an interface of the oil phase and the aqueous phase droplet.

2. The method of claim 1, wherein the aqueous phase droplet comprises a microorganism selected from the group consisting of carbon monoxide-utilizers, hydrogen utilizers, and alkane utilizers.

3. The method of claim 1, wherein the gas substrate is selected from the group consisting of carbon monoxide, hydrogen, and alkane.

4. The method of claim 1, wherein the aqueous phase droplet comprises a methanotroph, and wherein the gas substrate is methane.

5. The method of claim 4, wherein the methanotroph is adapted to produce a bioproduct of biodiesel generation, propylene oxide production, single cell protein production, extracellular polysaccharides production, or human health supplements production.

6. The method of claim 4, wherein the methanotroph is adapted to produce a polyhydroxyalkanoate, and the method further comprises recovering the polyhydroxyalkanoate produced.

7. The method of claim 1, wherein the oil phase comprises a fluid that has a higher solubility for the gas substrate than the aqueous phase and is capable of generating a stable emulsion with the aqueous phase.

8. The method of claim 1, wherein the oil phase comprises a hydrocarbon.

9. The method of claim 1, wherein the oil phase comprises a fluorocarbon.

10. The method of claim 1, wherein the oil phase comprises at least one of $C_9H_{50}F_{15}$ (HFE-7500), $C_{21}F_{48}N_2$ (FC-40), or perfluoromethyldecalin (PFMD).

11. The method of claim 1, wherein the emulsion is stabilized by a fluoro-surfactant comprising a poly(ethylene glycol)-perfluorinated polyether (PEG-PFPE) amphiphilic block copolymer.

12. The method of claim 1, wherein the emulsion is stabilized by a partially fluorinated silica nanoparticle.

13. The method of claim 12, wherein the aqueous phase droplet further comprises a hydrophilic polymer adsorbed to the partially fluorinated silica nanoparticle at the interface.

14. The method of claim 12, wherein the partially fluorinated silica nanoparticle is covalently grafted with a hydrophilic polymer.

15. The method of claim 1, wherein the method is substantially free of mechanical stirring or agitation of the emulsion during incubation.

16. The method of claim 1, wherein the aqueous phase droplet has a dimension greater than or equal to 50 nm and less than or equal to 1000 microns.

* * * * *